United States Patent
Ousley

(10) Patent No.: US 7,931,213 B2
(45) Date of Patent: Apr. 26, 2011

(54) PORTABLE SCENT DISPERSER

(76) Inventor: Lisa J. Ousley, Mansfield, OH (US)

( * ) Notice: Subject to any disclaimer, the term of this patent is extended or adjusted under 35 U.S.C. 154(b) by 258 days.

(21) Appl. No.: 12/186,349

(22) Filed: Aug. 5, 2008

(65) Prior Publication Data

US 2010/0032494 A1 Feb. 11, 2010

(51) Int. Cl.
*A24F 25/00* (2006.01)
*B67D 7/08* (2010.01)
*B05B 1/24* (2006.01)
*F24H 3/06* (2006.01)

(52) U.S. Cl. ............. 239/139; 239/34; 239/58; 239/71; 239/128; 239/135; 239/136; 392/356; 392/366

(58) Field of Classification Search ................ 239/13, 239/34, 35, 71, 72, 128, 135, 136, 139, 57, 239/58, 59; 422/120, 123, 124, 125; 392/356, 392/360, 366, 386, 390, 391; 219/209, 445.1; 416/95; 126/110 D
See application file for complete search history.

(56) References Cited

U.S. PATENT DOCUMENTS

| | | | |
|---|---|---|---|
| 6,443,434 B1 * | 9/2002 | Prather | 261/26 |
| 6,627,857 B1 | 9/2003 | Tanner et al. | |
| 6,783,117 B2 * | 8/2004 | Wohrle | 261/26 |
| 7,067,772 B2 | 6/2006 | Tanner et al. | |
| 7,132,084 B1 | 11/2006 | Roumpos | |
| 2003/0175171 A1 * | 9/2003 | Yamamoto et al. | 422/124 |
| 2008/0038156 A1 * | 2/2008 | Jaramillo | 422/124 |

* cited by examiner

*Primary Examiner* — Jason J Boeckmann
*Assistant Examiner* — Ryan Reis
(74) *Attorney, Agent, or Firm* — Dale J. Ream

(57) ABSTRACT

A portable scent dispensing device includes a base having a warming element for heating scented matter situated thereon, the warming element being configured for electrical communication with a power source. The dispensing device includes a first switch for actuating the warming element with the power source. A hood is directly above the base and includes a fan configured for electrical communication with the power source, the hood being separated from the base to allow the scented matter to be positioned upon the warming element. A first wall extends upwardly from the base and a second wall extends downwardly from the hood. At least one fastener maintains the hood at respective heights directly above the base by maintaining the second wall at respective positions relative to the first wall, wherein the first wall and the second wall collectively surround at least about halfway around the scented matter.

3 Claims, 5 Drawing Sheets

PORTABLE SCENT DISPERSER

BACKGROUND OF THE INVENTION

This invention relates generally to a scent disperser and, more particularly, to a flameless scent disperser that is battery powered, portable, and adjustable.

Flameless scent dispersers include a warming plate for heating a scented wax candle such that the scent is dispersed into the air. Traditional scent dispersers include an AC power cord and are, therefore, stationary devices. Accordingly, multiple scent dispersers may be situated about a home so that one is always available when and where desired by a user. In other words, a user may need to reposition electrical cords or even utilize extension cords when repositioning a scent disperser, depending on the location of the nearest AC wall outlet.

Various flameless scent dispersing devices are known in the art for dispersing scent from scented candles. Although assumably effective for their intended purposes, the existing devices are not portable, decorative, or adjustable for selectably varying scent dispersion.

Therefore, it would be desirable to have a portable scent dispersing device that utilizes battery power so as to be easily moved between locations without regard to the position of an AC power outlet. Further, it would be desirable to have a portable scent dispersing device that is adjustable and includes a fan for varying a degree of scent dispersion.

SUMMARY OF THE INVENTION

Therefore, a portable scent dispersing device according to a preferred embodiment of the present invention includes a base having a warming element for heating scented matter situated thereon, the warming element being configured for electrical communication with a power source. The dispersing device includes a first switch for actuating the warming element with the power source. A hood is directly above the base and includes a fan configured for electrical communication with the power source, the hood being separated from the base to allow the scented matter to be positioned upon the warming element. A first wall extends upwardly from the base and a second wall extends downwardly from the hood. The dispersing device includes at least one fastener for maintaining the hood at respective heights directly above the base by maintaining the second wall at respective positions relative to the first wall, wherein the first wall and the second wall collectively surround at least about halfway around the scented matter.

Therefore, a general object of this invention is to provide a scent disperser for heating a wax material and to disperse scent therefrom.

Another object of this invention is to provide a scent disperser, as aforesaid, that is portable and not dependent upon AC electrical power.

Still another object of this invention is to provide a scent disperser, as aforesaid, that includes a fan for increasing the dispersion of scent.

Yet another object of this invention is to provide a scent disperser, as aforesaid, having an adjustable length fan hood for selectably varying the dispersion of scent.

A further object of this invention is to provide a scent disperser, as aforesaid, having lighting features.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 3b is an isolated view on an enlarged scale taken from a portion of the portable scent disperser of FIG. 3a;

DESCRIPTION OF THE PREFERRED EMBODIMENT

A portable scent disperser will now be described in detail with reference to FIG. 1 through FIG. 5 of the accompanying drawings. More particularly, a portable scent disperser 100 includes a base 110 and a hood 120.

Figure 1:
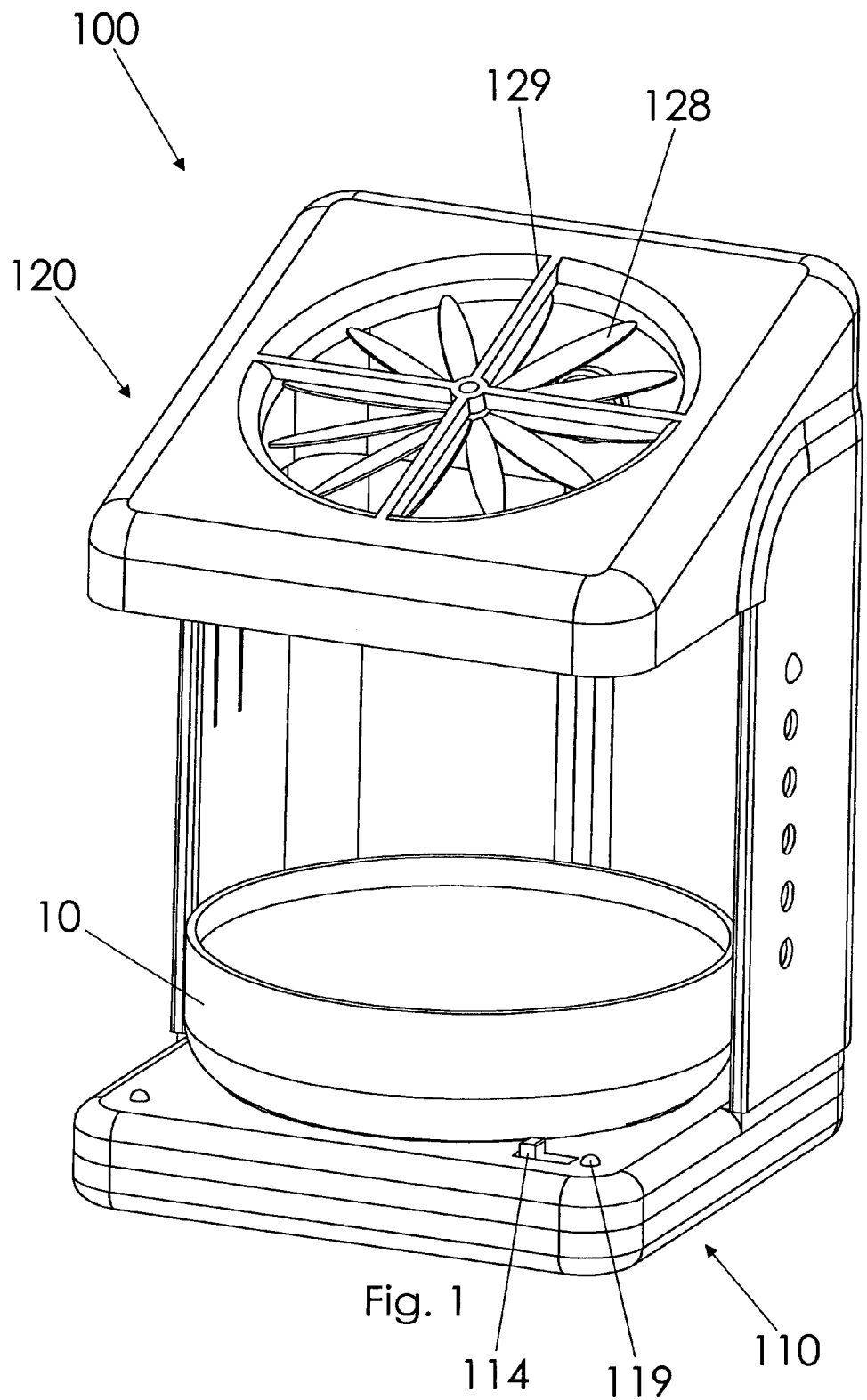
FIG. 1 is a perspective view of a portable scent disperser according to a preferred embodiment of the present invention.
Figure 2:
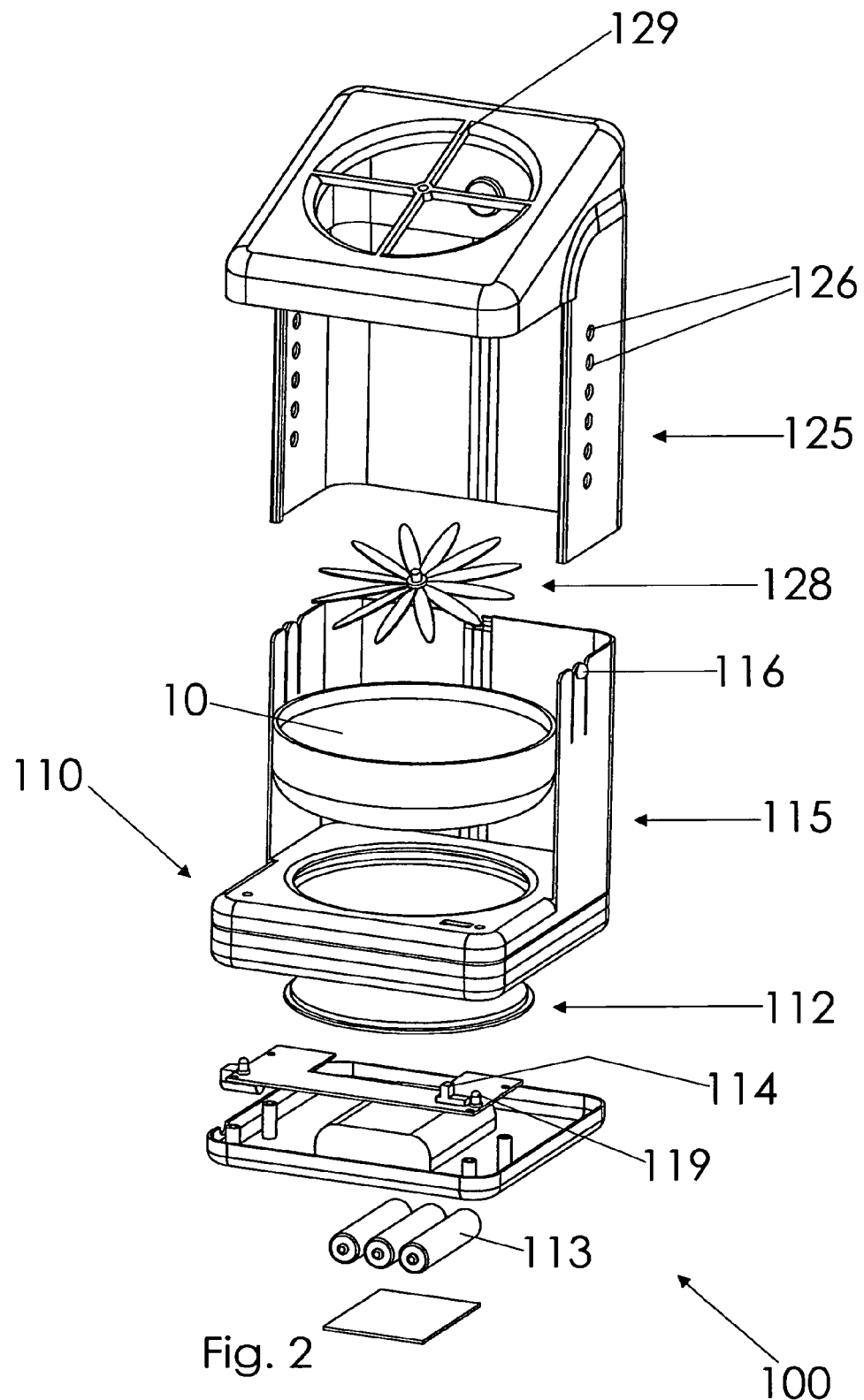
FIG. 2 is an exploded view of the portable scent disperser as in FIG. 1.
Figure 3A:
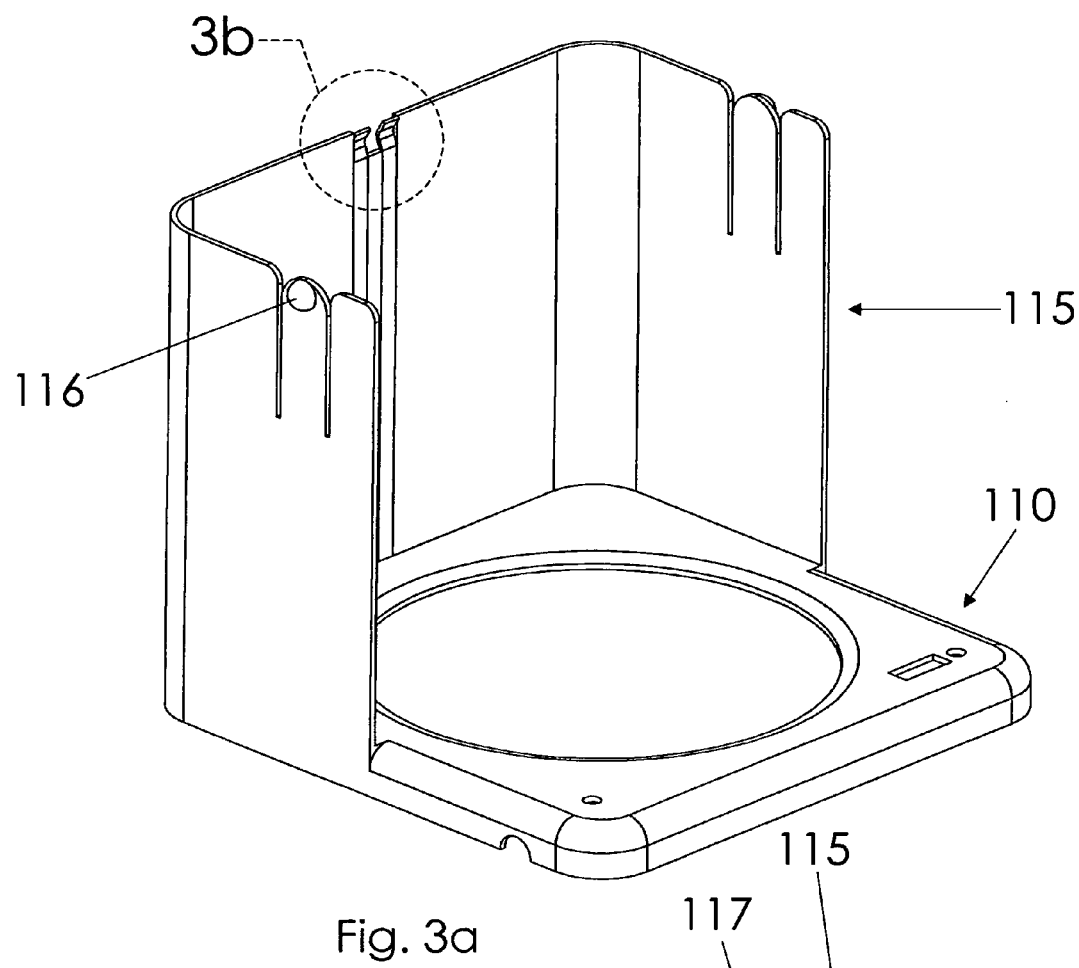
FIG. 3a is a perspective view of a base of the portable scent disperser as in FIG. 1 removed from the hood.
Figure 3B:
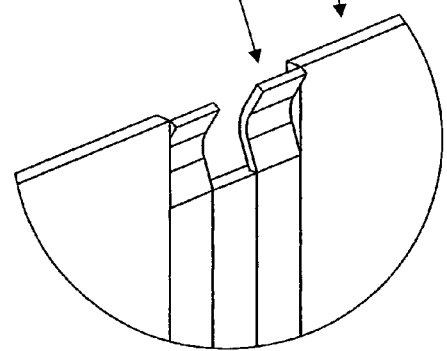
Figure 4:
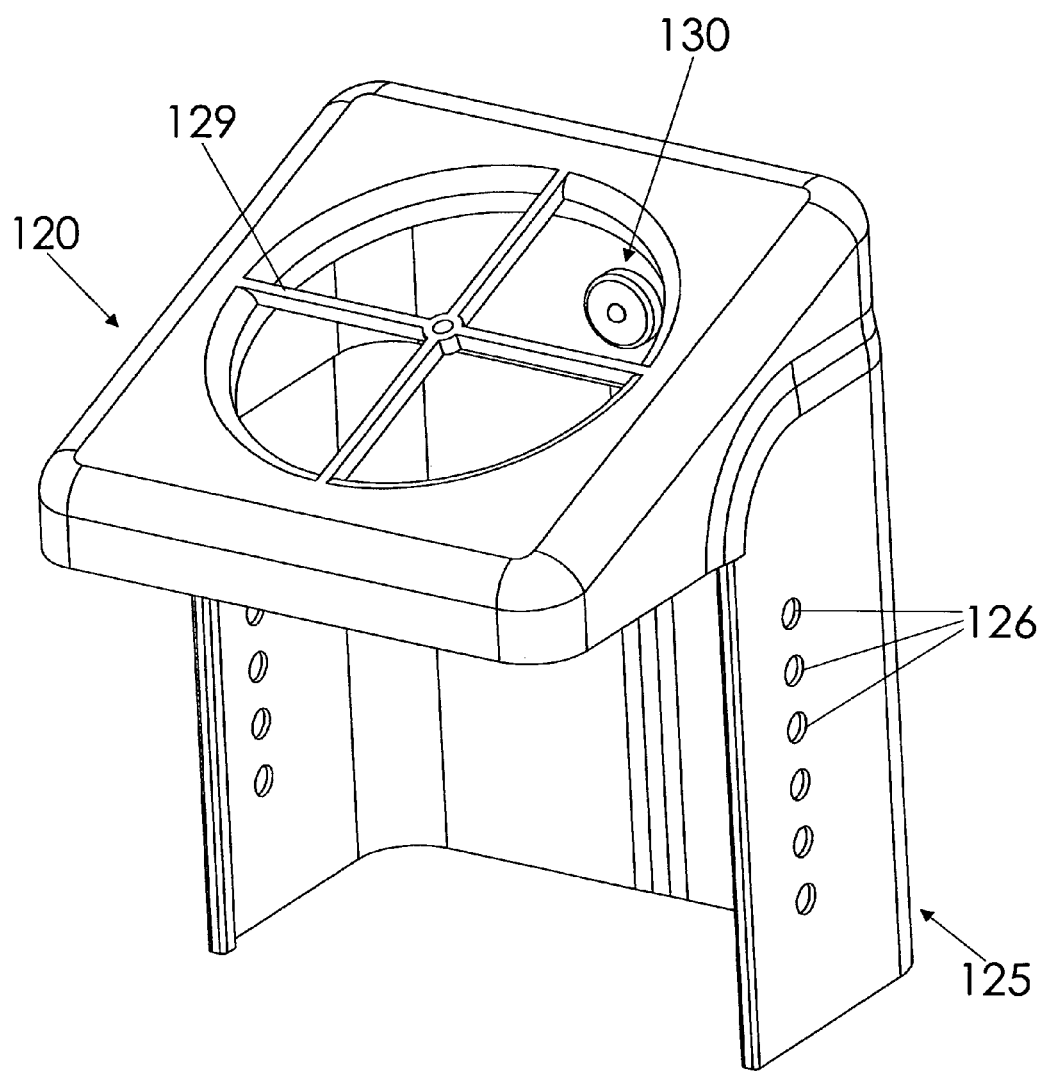
FIG. 4 is a perspective view of the hood removed from the base.

As shown in FIG. 2 and FIG. 3a, the base 110 has a warming element 112 for heating scented matter 10 (e.g., scented wax, scented gel, etc.) thereon. The warming element 112 is configured for electrical communication with a power source (e.g., a battery or a power grid). In a preferred embodiment, the warming element 112 is in electrical communication with a removable or rechargeable battery 113 (FIG. 2). A switch 114 (FIG. 1) is in electrical communication with the warming element 112 and the power source (e.g., the battery 113) to actuate the warming element with power source (e.g., the battery 113). The switch 114 may be manually operated (as shown in FIG. 1) or may be automatically actuated (e.g., by the placement of the scented matter 10 on the warming element 112). An indicator 119 may be in electrical communication with the switch 114 to indicate when the power source (e.g., the battery 113) is actuating the warming element 112. An automatic shutoff element (e.g., that uses a timer or a thermostat) may be included for deactivating the warming element 112 upon a predetermined condition occurring (e.g., an amount of time passing or the warming element 112 reaching a certain temperature).

Figure 5:
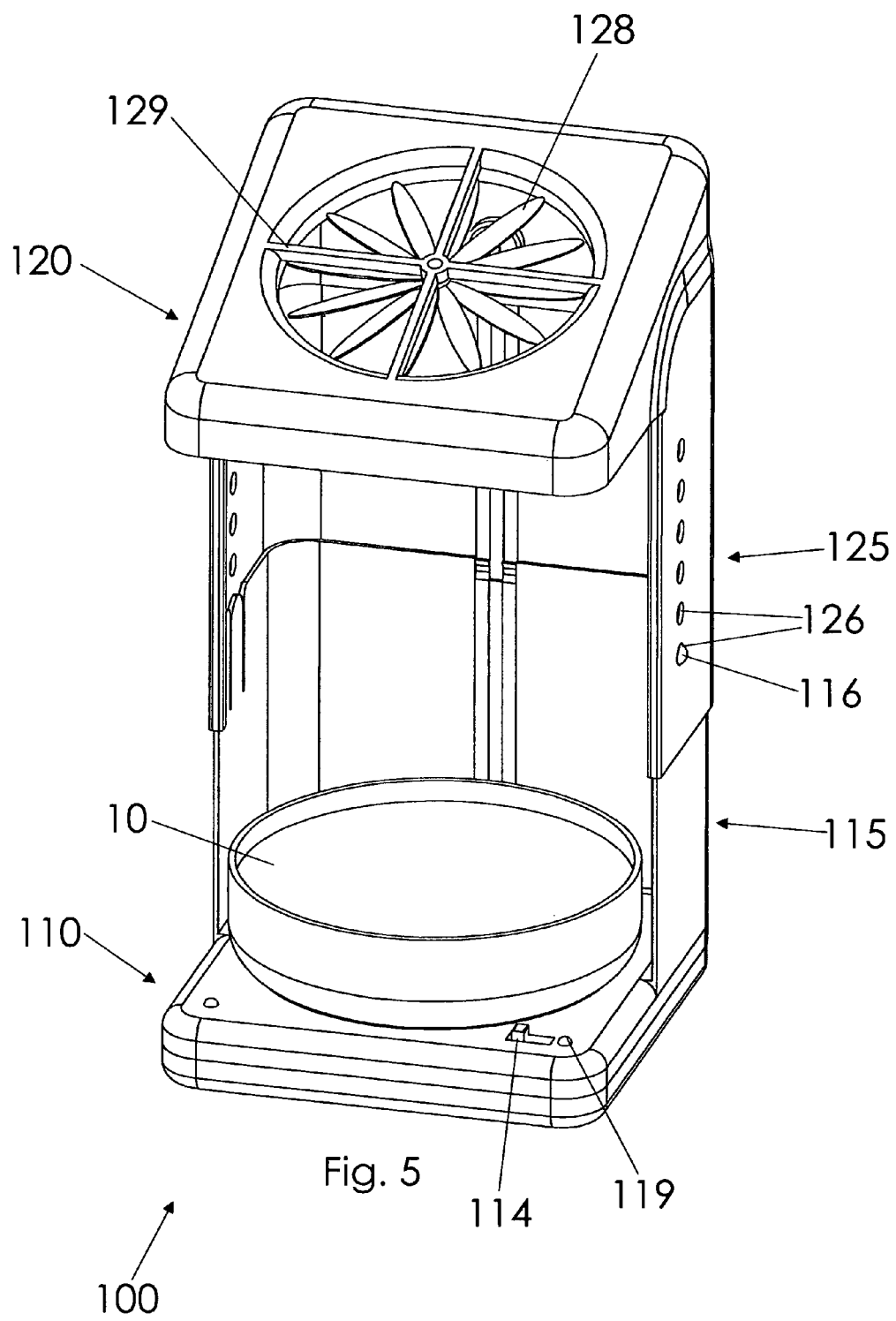
FIG. 5 is a perspective view of the portable scent disperser in a raised configuration.

The hood 120 is above the base 110 and is separated from the base 110 to allow the scented matter 10 to be positioned upon the warming element 112, as shown in FIG. 1. As shown in FIG. 2 a first wall 115 may extend upwardly from the base 110, and a second wall 125 may extend downwardly from the hood 120. Means for maintaining the hood 120 at respective heights above the base 110 by maintaining the second wall 125 at respective positions relative to the first wall 115 may be included. For example, a fastener (e.g., a protrusion 116 complementary to a plurality of holes 126) may be used to maintain the second wall 125 at various positions relative to the first wall 115. FIG. 1 shows an exemplary lowered position, and FIG. 5 shows an exemplary raised position. In some embodiments, the first wall 115 and/or the second wall 125 surround at least about halfway around the scented matter 10 (FIG. 1). A lock 117 (FIG. 3b) may bias the walls 115, 125 from separating. More particularly, the lock 117 may include one or more tabs positioned along an upper edge of the first wall 115 that may bear against the second wall 125 and contribute to smooth raising and lowering of the walls without separation thereof.

The hood 120 may include a fan 128 (FIGS. 1 and 2) that is configured to be in electrical communication with either the power source powering the warming element 112 (i.e., the battery 113) or another power source. As shown in FIG. 1, the warming element 112 may extend generally horizontally, and the fan 128 may be angularly offset from the warming element 112. A guard 129 (FIGS. 1 and 2) may be adjacent the fan 128 to restrict access to the fan 128 (i.e., for user safety). The fan 128 is in electrical communication with the switch 114 or another switch for actuating the fan 128 with the attached power source.

Means may be included for providing light of a plurality of tints. For example, a light device 130 (FIG. 4) may include a plurality of different colored lights (e.g., LED's) or a light with a plurality of different colored filters. Various means for selecting a light tint may also be included. In some embodiments, an automated data input device may obtain data from the scented matter to select the light tint by using RFID, bar code, or other data transfer technology, for example. In other embodiments, a switch may be included to allow the user to select the light tint. Especially if the light tint is automatically selected, the light tint may be associated with the scented matter 10 (e.g., cinnamon-scented matter 10 may be associated with a red tint, green apple-scented matter 10 may be associated with a green tint, etc.). An audio device may be included for outputting sounds when activated, and the sounds may be changed or supplemented through any acceptable data transfer method, or the sounds may be unalterable. The audio device may be associated with any switch set forth above or another switch.

In use, the scented matter 10 may be placed on the warming element 112, and the warming element 112 may be activated by the switch 114 to warm the scented matter 10. If necessary, the height of the hood 120 may be adjusted before the scented matter 10 is placed on the warming element 112 by adjusting the position of the walls 115, 125, as set forth above. The fan 128 may be activated (e.g., by the switch 114 or another switch) and may direct the scent from the warmed scented matter 10 to a desired location. By collectively surrounding at least about halfway around the scented matter 10, the walls 115, 125 may channel the scent from the warmed scented matter 10 to the fan 128. The light device 130 may accentuate the scent dispersion and may be activated by the switch 114 or another switch. As set forth above, the light device may include a plurality of different colored tints, and a tint may be selected in various ways. Similarly, the audio device may accentuate the scent dispersion and may be activated by the switch 114 or another switch. The automatic shutoff element may deactivate the warming element 112, or the switch 114 may be used to deactivate the warming element 112. The use of battery 113 may allow the portable scent disperser 100 to be easily moved and positioned as desired.

It is understood that while certain forms of this invention have been illustrated and described, it is not limited thereto except insofar as such limitations are included in the following claims and allowable functional equivalents thereof.

The invention claimed is:

1. A portable scent disperser, comprising:
a base having a warming element for heating scented matter thereon, said warming element being configured for electrical communication with a power source;
a first switch for actuating said warming element with said power source;
a hood directly above said base, said hood including a fan attached thereto configured for electrical communication with said power source or another power source, said hood being separated from said base to allow said scented matter to be positioned upon said warming element;
a first wall extending upwardly from said base;
a second wall extending downwardly from said hood and defining a plurality of holes;
at least one fastener positioned on said first wall that includes a configuration that is complementary to said plurality of holes and selectively receivable therein for maintaining said hood at a selectable height directly above said base by maintaining said second wall at selected positions relative to said first wall;
a locking tab positioned on said first wall that is biased to bear against said second wall to prevent separation of said walls;
wherein said first wall and said second wall collectively surround at least about halfway around said scented matter;
wherein:
said warming element extends generally horizontally;
said fan is angularly offset from said warming element;
means for providing light of a plurality of tints;
means for selecting a said tint; and
an audio device for outputting sounds associated with said scented matter when activated; and
means for selecting said associated sound.

2. The portable scent disperser of claim 1, further comprising:
an indicator in electrical communication with said first switch to indicate when said warming element is actuated; and
an automatic shutoff element for deactivating said warming element.

3. The portable scent disperser of claim 1, wherein said means for selecting a said tint includes an automated data input device for obtaining data from said scented matter.

* * * * *